US008609907B2

(12) United States Patent
Eicher et al.

(10) Patent No.: US 8,609,907 B2
(45) Date of Patent: Dec. 17, 2013

(54) PROCESS FOR THE PREPARATION OF CHLOROFLUOROALKENES

(75) Inventors: Johannes Eicher, Sehnde (DE); Wolfgang Kalbreyer, Steyerberg (DE); Ercan Uenveren, Hannover (DE)

(73) Assignee: Solvay Fluor GmbH, Hannover (DE)

( * ) Notice: Subject to any disclaimer, the term of this patent is extended or adjusted under 35 U.S.C. 154(b) by 245 days.

(21) Appl. No.: 13/129,985

(22) PCT Filed: Nov. 20, 2009

(86) PCT No.: PCT/EP2009/065565
§ 371 (c)(1),
(2), (4) Date: May 18, 2011

(87) PCT Pub. No.: WO2010/060868
PCT Pub. Date: Jun. 3, 2010

(65) Prior Publication Data
US 2011/0224464 A1    Sep. 15, 2011

(30) Foreign Application Priority Data

Nov. 25, 2008 (EP) .................................... 08169859

(51) Int. Cl.
*C07C 17/25* (2006.01)

(52) U.S. Cl.
USPC ............................ 570/156; 570/135; 570/155

(58) Field of Classification Search
None
See application file for complete search history.

(56) References Cited

U.S. PATENT DOCUMENTS

| | | | |
|---|---|---|---|
| 2,673,139 A * | 3/1954 | Woolf et al. .................. | 423/489 |
| 3,118,005 A * | 1/1964 | Pavlath et al. ................ | 570/156 |
| 5,243,103 A | 9/1993 | Lerot et al. | |
| 5,739,406 A | 4/1998 | Pennetreau et al. | |
| 6,399,839 B1 | 6/2002 | Mathieu et al. | |
| 6,399,840 B1 | 6/2002 | Schoebrechts et al. | |
| 6,441,256 B1 | 8/2002 | Mathieu et al. | |
| 6,452,057 B1 | 9/2002 | Lambert et al. | |
| 6,521,803 B1 | 2/2003 | Lambert et al. | |
| 6,730,817 B1 | 5/2004 | Wilmet et al. | |
| 6,930,215 B2 | 8/2005 | Wilmet et al. | |
| 7,074,434 B2 | 7/2006 | Lambert et al. | |
| 7,223,892 B2 | 5/2007 | Lambert et al. | |
| 7,566,809 B2 | 7/2009 | Lambert et al. | |
| 2005/0256348 A1 | 11/2005 | Wilmet et al. | |
| 2006/0052649 A1 | 3/2006 | Kemnitz et al. | |
| 2007/0129579 A1* | 6/2007 | Wang et al. .................... | 570/155 |

FOREIGN PATENT DOCUMENTS

| | | |
|---|---|---|
| EP | 1440939 A1 | 7/2004 |
| EP | 1666411 A1 | 6/2006 |
| FR | 1312185 A | 12/1962 |
| WO | WO 2005037902 A1 | 4/2005 |
| WO | WO 2006058794 A1 | 6/2006 |
| WO | WO 2008040803 A1 | 4/2008 |
| WO | WO 2009010472 A1 | 1/2009 |
| WO | WO 2010055146 A2 | 5/2010 |

OTHER PUBLICATIONS

Fields, R., et al, "Cyclopropane Chemistry. Part I. Thermal Isomerisation of gem-Dichlorocyclopropanes to olefins", Journal of the Chemical Society C: Organic, 1, 1969, XP002560671, pp. 165-172 1969.
U.S. Appl. No. 12/442,900, filed Mar. 25, 2009, Veronique Mathieu, et al.
U.S. Appl. No. 12/668,568, filed Jan. 11, 2010, Ercan Uenveren, et al.
U.S. Appl. No. 13/128,594, filed May 10, 2011, Ercan Uenveren, et al.
U.S. Appl. No. 09/051,746, filed Jun. 8, 1998, Vincent Wilmet, et al.
U.S. Appl. No. 10/613,546, filed Jul. 3, 2003, Vincent Wilmet, et al.
U.S. Appl. No. 09/423,258, filed Dec. 30, 1999, Jean-Paul Schoebrechts, et al.
U.S. Appl. No. 09/868,368, filed Jul. 17, 2001, Alain Lambert, et al.
U.S. Appl. No. 10/282,785, filed Oct. 29, 2002, Alain Lambert, et al.
U.S. Appl. No. 11/476,306, filed Jun. 28, 2006, Alain Lambert, et al.
U.S. Appl. No. 11/753,970, filed May 25, 2007, Alain Lambert, et al.
U.S. Appl. No. 09/677,125, filed Sep. 29, 2000, Alain Lambert, et al.

* cited by examiner

*Primary Examiner* — Sudhakar Katakam
(74) *Attorney, Agent, or Firm* — Beatrice C. Ortego

(57) ABSTRACT

One or more hydrochlorofluoroalkenes can be produced by dehydrofluorination of a hydrochlorofluoroalkane over a X-ray amorphous high surface metal fluoride or a X-ray amorphous or weakly crystalline metal oxide fluoride wherein the metal is selected from the $2^{nd}$, $3^{rd}$ or $4^{th}$ main group or any subgroup of the periodic system of elements. High-surface aluminum fluoride or aluminum oxide fluoride are especially suitable as catalysts. For example, $CF_3CH_2CHClF$ is reacted to produce $CF_3CH=CHCl$, and $CF_3CH_2CClFCH_3$ is reacted to form $CF_3CH_2CCl=CH_2$ and/or $CF_3CH=CClCH_3$.

20 Claims, No Drawings

PROCESS FOR THE PREPARATION OF CHLOROFLUOROALKENES

CROSS-REFERENCE TO RELATED APPLICATIONS

This application is a U.S. national stage entry under 35 U.S.C. §371 of International Application No. PCT/EP2009/065565 filed Nov. 20, 2009, which claims priority to European Application No. 08169859.9 filed Nov. 25, 2008, this application being herein incorporated by reference in its entirety for all purposes.

The present invention concerns a process for the preparation of chlorofluoroalkenes and certain chlorofluoroalkenes obtainable thereby.

Chlorofluoroalkenes are intermediates in chemical synthesis. They are, for example, monomers and can be polymerized, see WO2005/037902. They can be reacted with hydrogen to provide the respective fluoroalkenes, see U.S. Pat. No. 5,243,103.

Object of the present invention is to provide a process for the preparation of chlorofluoroalkenes. Another object is to provide novel chlorofluoroalkenes.

These and other objects are attained by the process of the present invention and the specific chlorofluoroalkenes given in the claims.

The present invention provides a process for the preparation of hydrochlorofluoroalkenes from hydrochlorofluoroalkanes by contacting said hydrochlorofluoroalkanes with X-ray amorphous high surface metal fluoride or X-ray amorphous or weakly crystalline metal oxide fluoride wherein the metal is selected from the $2^{nd}$, $3^{rd}$ or $4^{th}$ main group or any subgroup of the periodic system of elements. One or more molecules of HF are split off from the respective hydrochlorofluoroalkanes, and thus, a hydrochlorofluoroalkene or hydrochlorofluoroalkadiene or triene or even polyene is formed.

In one embodiment, the catalyst is a full catalyst. In another embodiment, the catalyst is carried on a support.

Lewis-acidic metal fluorides are preferred, especially aluminium fluorides, chromium fluorides and iron fluorides. Aluminium fluoride and aluminium oxide fluoride are preferred as catalyst. Aluminium fluoride is especially preferred as catalyst (if desired, carried on a support).

In the context of the present invention, the terms "amorphous" and "X-ray amorphous" are interchangeable.

The metal fluorides have certain novel characteristics when compared with fluorides of the state of the art. They preferably have an active surface of about 100-300 $m^2/g$ (measured with $N_2$, e.g. in a micromeritics ASAP 2001). They are strong Lewis acids. They are essentially free of chloride. The amorphous metal fluoride is X-ray amorphous; it is highly distorted. The term "X-ray amorphous metal fluoride" denotes that the microcrystalline domains of the solid matter, i.e. the amorphous metal fluoride, have a size of less than 20 nm. They have a mesoporous surface, as revealed by REM (Reflection Electron Microscopy). These features especially apply to amorphous aluminium fluoride. The amorphous aluminium fluoride has a strongly distorted structure of the $AlF_3$ octahedron. These disorders are responsible for the X-ray amorphous condition of the solid matter. The quadrupol coupling constant QCC is about 1.5 MHz. In the IR spectrum, rather only a single very broad band ($v_3$ of Al—F at 667 $cm^{-1}$) is observed as can be allocated to the amorphous rather the crystalline structure. A single broad band for the valence vibration $v_3$ of Al—F at 667 $cm^{-1}$ indicates an amorphous structure. The increased Lewis acidity can be demonstrated by pyridine absorption and $NH_3$-TPD ($NH_3$ temperature programmed desorption). The X-ray amorphous catalysts, especially $AlF_3$, have the advantage that they are not hygroscopic.

Such high surface area aluminium fluoride (HS-$AlF_3$), as well as other high surface are metal fluorides, can be synthesized as described in US 2006/0052649 or EP 1440939 A1 (method for the preparation of amorphous metal fluorides), and EP 1666411 A1 (method for the preparation of X-ray amorphous or weakly crystalline metal oxide fluorides and new uses thereof).

Amorphous or weakly crystalline metal oxide fluoride is the same as highly distorted metal oxide fluoride. "X-ray amorphous" preferably means that the X-ray diffraction pattern shows no peaks.

Amorphous metal fluoride is preferred as dehydrofluorinating catalyst. It can be prepared as described in EP 1440939 A1. Amorphous high surface area aluminium fluoride (or other high surface area metal fluorides) is prepared by a method comprising the steps of a) providing a precursor, whereby the precursor comprises a structure having a formula of $M^{x+}F_{(x-\delta)-y}B_yL_d$; and
b) reacting the precursor with a fluorinating agent generating the amorphous metal fluoride having a formula of $M^{x+}F_{x-\delta}$);

whereby M is a metal of the $2^{nd}$, $3^{rd}$ or $4^{th}$ main group or any metal from a sub-group of the periodic system of the elements, preferably aluminium; B is a co-ordinately bound group; x is in case of aluminium 3; y is any integer between 1 and 3; $\delta$ is 0 to 0.1; and x-$\delta$>y.

B is preferably an alkoxide, enolate or carboxylic acid group, more preferably an alkoxide of the formula —O—$C_cH_{2c+1}$ wherein c is any integer from 1 to 6; L is a solvent, preferably an anhydrous organic solvent selected from the group comprising alcohols, ethers, ketones, alkanes, aromatics; and d is ≤1.

According to EP 1440939 A1, the precursor is obtained by reacting $M^{x+}B_x$, wherein B is preferably an alkoxide, if the metal M is aluminium, B is more preferably propoxide, dissolved or suspended in an organic solvent L, with 2 to 4 equivalents, preferably 3 equivalents, anhydrous HF, preferably dissolved in an organic solvent L', whereby L' can be any of the solvents L and also L' can be equal to L; followed by removing excessive solvents under vacuum at temperatures equal to or less than 350° C., preferably equal to or less than 200° C., still more preferably equal to or less than 100° C.; providing a precursor as defined above.

The preparation of the precursor is preferably performed in a waterfree solvent, preferably selected from the group consisting of alcohols, ethers, ketones, alkanes, petroleum ether, formic acid, acetic acid or propionic acid. Alcohols of formula $C_cH_{2c+1}OH$ with c=1 to 6, especially 1 to 3, are preferred.

The precursor obtained thereby, in a second step, is further fluorinated, "activated", whereby gaseous fluorinating agents are used at elevated temperatures, preferably hydrofluorocarbons or hydrofluorochlorocarbons, especially $CHClF_2$ or $CH_2F_2$ at temperatures between up to 350° C., or gaseous HF at temperatures from 50° C. up to 300° C., preferably at 75° C. up to 150° C. The fluorinating agent is preferably admixed with an inert gas such as nitrogen or argon, whereby up to 95 Vol.-% inert gas can be used; providing an amorphous metal fluoride as defined above, whereby in case of activation with HF the obtained metal fluoride, specifically if the metal is aluminium, can contain adsorbed HF, which can be removed by subsequent exposure to an inert gas stream at temperatures up to 250° C.

In a preferred embodiment, the amorphous high surface metal fluoride consists essentially of aluminium fluoride. The term "essentially" denotes preferably that the content of other amorphous metal fluorides is equal to or less than 3% by weight, still more preferably equal to or less than 2% by weight.

EP 1440939 A1 discloses another embodiment wherein $M^{x+}F_{(x-\delta)-y}B_y$ is used as starting material, and which is not coordinated with a solvent.

In another embodiment, if desired, the aluminium fluoride can be doped with metal fluorides of zinc, tin, copper, chromium, vanadium, iron, or magnesium.

The details given above concern a full catalyst. In an alternative, the catalyst can be used in the form of a supported catalyst. As is well known, this denotes preferably a catalytic coating on a carrier or support. High surface area metal fluoride catalysts and X-ray amorphous or weakly crystalline metal oxide fluoride wherein the metal is selected from the $2^{nd}$, $3^{rd}$ or $4^{th}$ main group or any subgroup of the periodic system of elements, supported on a carrier, and their preparation is disclosed in the not yet published international patent application PCT/EP2008/059112 the content of which is incorporated herein by reference.

The supported catalysts can be prepared as follows:

High surface X-ray amorphous metal fluoride on a support, preferably with the exception of $MgF_2$ as support, is novel and another aspect of the present invention. The supported highly Lewis acidic catalysts the catalytic activity of which for the tested dehydro fluorination reactions are similar to that of the known bulk catalyst (which is not concerned in the context of the present invention). In principle, the metal can be selected from the $2^{nd}$, $3^{rd}$ or $4^{th}$ group or the sub groups of the periodic system of the elements. Of course, if desired, the supported catalyst may comprise mixed amorphous metal fluorides. Preferred amorphous metal fluorides are those of Al, Cr, Fe, V, Ga and Mg. Amorphous aluminium fluoride is the preferred metal fluoride also for the supported catalysts. Preferably, a support is selected which has a suitably shaped form, is chemically and thermally stable under the conditions of catalyst synthesis and under reaction conditions of catalyst use, mechanically stable, not deteriorating the performance of the catalyst, not interfering with the catalysed reaction, and enabling anchoring of $HS-AlF_3$. Any support which meets these requirements can be used. For example, oxides, fluorides and oxifluorides of aluminium or of transition metals are very suitable. Usually, these are present in crystalline form. Activated carbon can also be applied; in a preferred embodiment, aluminium oxide or aluminium fluoride is used as support; in a more preferred embodiment aluminium oxide is used, and in an even more preferred embodiment $\gamma-Al_2O_3$ is used as support. In this case, the supported metal fluoride is high surface metal fluoride on $\gamma-Al_2O_3$.

Very preferably, the supported amorphous metal fluoride catalyst is $HS-AlF_3$ on a support, e.g., $HS-AlF_3$ on $\gamma-Al_2O_3$. If desired, the aluminium fluoride can be doped with one or more other metal fluorides, for example, the fluorides of zinc, tin, copper, iron, chromium, vanadium or magnesium. Such doped supported catalysts can be prepared by adding hydrolysable metal compounds, for example, the metal alkoxides to the hydrolysable aluminium compound.

Preferably, the total amount of coated amorphous metal fluoride, especially of $AlF_3$ in the supported catalyst is equal to or greater than 3% by weight, more preferably equal to or more than 4% by weight. Preferably, the content of aluminium fluoride in the supported catalyst is equal to or less than 30% by weight, more preferably equal to or less than 20% by weight. In some applications, the content can be equal to or less than 10% by weight. A range with good results, e.g. in dehydrofluorination reactions, is between 4 and 20% by weight. A range of 4 to 8% by weight also gives good results.

In the following, the preparation of amorphous metal fluorides, especially amorphous aluminium fluoride ($HS-AlF_3$), supported on a carrier, will be described. The terms "carrier" and "support" are interchangeable in the frame of the present invention.

The synthesis of the high surface area aluminium fluoride ($HS-AlF_3$), coating, as well as coatings of other high surface are metal fluorides, can be performed analogously as described in US 2006/0052649 or EP 1440939 A1 (method for the preparation of amorphous metal fluorides), and EP 1666411 A1 (method for the preparation of X-ray amorphous or weakly crystalline metal oxide fluorides and new uses thereof). A coating of amorphous metal fluoride as described in EP 1440939 A1 is preferred. In a preferred embodiment, the amorphous high surface metal fluoride consists essentially of aluminium fluoride. The term "essentially" denotes preferably that the content of other amorphous metal fluorides in the coating is equal to or less than 3% by weight, still more preferably equal to or less than 2% by weight.

The synthesis of supported high surface area metal fluoride on a support, preferably aluminium fluoride on a support ($HS-AlF_3$/support), follows basically the synthesis route outlined for $HS-AlF_3$ in EP 1440939 A1 and above extended by a step of anchoring to a suitable support at an appropriate stage of $HS-AlF_3$ synthesis.

It is known from EP 1666411 A1 that the Lewis acidity of amorphous high surface area aluminium fluoride becomes reduced upon partial substitution of fluoride by oxide, consequently, if formation of oxide fluoride is to be avoided, reducing adsorbed water and/or inherent OH-groups of the support by thermal pre-treatment preserves the Lewis acidity, i.e. the catalytic performance of the anchored $HS-AlF_3$, i.e. of the final catalyst. Therefore, the support, e.g. $\gamma-Al_2O_3$, is preferably heated prior to the coating procedure. Heating is preferably performed for equal to or less than 48 hours, preferably equal to or less than 12 hours, advantageously at temperatures which do not result in undesired transformation of the support. For example, it is avoided to transform $\gamma-Al_2O_3$ into $\alpha-Al_2O_3$ (which can be determined by X-ray powder diffraction). For example, $\gamma-Al_2O_3$ can be heated to temperatures between 400° C. and 900° C. Preferably, it is heated to a temperature equal to or higher than 600° C. Preferably, it is heated to a temperature equal to or lower than 900° C. in air and subsequently cooled down to room temperature under exclusion of moisture.

According to this aspect of the present invention, amorphous high surface area metal fluoride is prepared by a method comprising the steps of a) providing a precursor coated on a support, whereby the precursor comprises a structure having a formula of $M^{x+}F_{(x-\delta)-y}B_yL_d$; and b) reacting the precursor with a fluorinating agent generating the amorphous metal fluoride having a formula of $M^{x+}F_{x-\delta)}$ on a support;

whereby M is a metal of the $2^{nd}$, $3^{rd}$ or $4^{th}$ main group or any metal from a sub-group of the periodic system of the elements, preferably aluminium; B is a co-ordinately bound group; x is in case of aluminium 3; y is any integer between 1 and 3; δ is 0 to 0.1; and x-δ>y.

B is preferably an alkoxide, enolate or carboxylic acid group, more preferably an alkoxide of the formula —O—$C_cH_{2c+1}$ wherein c is any integer from 1 to 6; L is a solvent, preferably an anhydrous organic solvent selected from the group comprising alcohols, ethers, ketones, alkanes, aromatics; and d is ≤1. In one embodiment, d is 0.

The preparation of the supported precursor is preferably performed in a waterfree solvent, preferably selected from the group consisting of alcohols, ethers, ketones, alkanes, petroleum ether, formic acid, acetic acid or propionic acid. Alcohols of formula $C_cH_{2c+1}OH$ with c=1 to 6, especially 1 to 3, are preferred.

The precursor can be obtained by reacting $M^{x+}B_x$, wherein B is preferably an alkoxide, if the metal M is aluminium, B is more preferably propoxide, dissolved or suspended in an organic solvent L, with anhydrous HF, preferably dissolved in an organic solvent L', whereby L' can be any of the solvents L and also L' can be equal to L. This is a sol-gel type reaction.

The method to apply a coating of the precursor on the support will now be explained in detail for the preferred embodiment of amorphous aluminium fluoride as supported catalyst.

The coating procedure can be performed in a manner principally known to prepare catalytic coatings on catalyst supports. Two specific alternatives are preferred. Both alternatives comprise a step a) or—as concerns the second alternative—b) wherein a support coated with the precursor $M^{x+}F_{(x-\delta)-y}B_yL_d$ or $M^{x+}F_{(x-\delta)-y}B_y$ is formed, and a step c) wherein the activation takes place.

Alternative a): According to the first preferred alternative, the support is impregnated with the aluminium compound $M^{x+}B_x$; M, B, x and y have the meanings given above. After impregnation, the sol-gel reaction with HF, preferably applied in a solvent, is performed to obtain the precursor.

In detail, the support, preferably thermally pretreated γ-Al$_2$O$_3$, is given, preferably under stirring, to a solution of a suitable organic aluminium compound, preferably an aluminium alkoxide, more preferably aluminium isopropoxide or methoxide, in an anhydrous organic solvent, preferably an alcohol. If a doped supported catalyst is to be produced, a suitable organic metal compound of the respective metal or metals is added. Contact between support and aluminium compound, preferably under stirring, is continued for a sufficient time to achieve the desired degree of impregnation. For example, after addition of the aluminium compound, the contact can be continued for equal to or more than 10 minutes, preferably, for equal to or more than 20 minutes. The contact can be extended, if desired, to a very long time, for example, more than 6 hours. It is assumed that the longer the contact, the deeper the aluminium compound or precursor will penetrate into the support. Preferably, the contact between support and aluminium compound is equal to or less than 6 hours, still more preferably, equal to or less than 2 hours. Often, 20 minutes to 45 minutes are very suitable.

Then, $M^{x+}B_x$ (here, M is preferably Al) is reacted with HF to transform it into the precursor. A solution of anhydrous hydrogen fluoride in an organic solvent, preferably in an C1 to C3 alcohol or in diethyl ether, is added, preferably under continued stirring, to the system of support and aluminium compound $M^{x+}B_x$ (M=Al). The amount of HF is selected so that the molar ratio of HF:Al is preferably equal to or greater than 2. Preferably, it is equal to or lower than 4. Very preferably, the molar ratio of HF:Al is 3±0.1. Most preferably, the molar ratio is 3. Preferably, the total amount of aluminium compound starting material (which is converted to the HS-AlF$_3$ phase) in the system is adjusted to correspond to an AlF$_3$ content of the final catalyst of equal to or greater than 3% by weight, more preferably equal to or more than 4% by weight. Preferably, the content of aluminium fluoride in the supported catalyst is equal to or less than 30% by weight, more preferably equal to or less than 20% by weight, sometimes even equal to or less than 10% by weight. Often, the amount is adjusted so that the content of the HS-AlF$_3$ phase in the supported catalyst is between A highly preferred range is between 4 and 20% by weight. Often, a supported catalyst with 4 to 8% by weight HS-AlF$_3$ is produced.

Alternative b): According to the second preferred alternative, the organic metal compound, preferably the aluminium compound, preferably in the form of a solution, is first reacted in the sol-gel type reaction with the appropriate amount of HF solution, preferably under stirring, followed by addition of the respective support, whereby the materials used and their relative amounts are as described above, especially in view of the alternative a).

After the reaction of the aluminium compound and HF to form the precursor has taken place, be it after impregnation of the carrier according to the first alternative, or before contact with the carrier according to the second alternative, excessive solvent(s) is or are removed. Preferably, this is performed in a gentle manner, preferably under vacuum. The removal advantageously is supported by warming or heating. Preferably, the temperature is equal to or higher than 25° C., more preferably, it is equal to or higher than 30° C. Preferably, the temperature is equal to or lower than ≤200° C., more preferably, it is equal to or lower than 150° C. A preferred range is 40 to 90° C. Both procedures a) or b) and subsequent solvent removal provide a supported precursor, which, if γ-Al$_2$O$_3$ is used as support, can be described best by the formula of $M^{x+}F_{(x-\delta)-y}B_yL_d$/γ-Al$_2$O$_3$, or, according to the other embodiment of EP 1440939, is $M^{x+}F_{(x-\delta)-y}B_y$/γ-Al$_2$O$_3$, with M, F, x, y, δ, B, L and d as given above.

The precursor already has catalytic activity. The catalytic activity can be greatly enhanced if the precursor is activated by subsequent fluorination with a gaseous fluorinating agent at elevated temperature, for example, with one or more hydrochlorofluorocarbons or hydrofluorocarbons, especially with 1 or 2 carbon atoms, or with HF. The fluorinating agent is preferably admixed with an inert gas such as nitrogen or argon, whereby 10 up to 95 vol % inert gas can be used. In a preferred manner, the activation is performed applying A1) CHClF$_2$ or CH$_2$F$_2$ or CHF$_3$ or CH$_3$F, or
A2) gaseous HF; followed optionally by
B) flushing with inert gas, preferably nitrogen or a noble gas, for example, argon,
providing a highly Lewis acidic supported HS-AlF$_3$ catalyst, preferably on γ-Al$_2$O$_3$ of the formula AlF$_{3-\delta}$/γ-Al$_2$O$_3$.

In step A1), CHClF$_2$ is the preferred fluorinating agent. It can be applied in admixture with preferably mixed with up to 95% (v/v), of an inert gas such as nitrogen or a noble gas, preferably argon; the content of the inert gas is preferably equal to or higher than 75% (v/v); it is preferably equal to or lower than to 90% (v/v). Especially preferably, the inert gas content is 83±2% (v/v). The temperature in step A1) preferably is equal to or higher than 250° C., more preferably, equal to or higher than 300° C. Preferably, the temperature is equal to or lower than 400° C. 340° C. to 360° C. is a very preferred range.

In the alternative step A2) wherein HF is used as fluorinating agent, the temperature during treatment is preferably equal to or lower than 200° C.; preferably, it is equal to or higher than 90° C. A temperature range from 75° C. to 150° C. is very preferred, still more a range from 110° C. to 130° C. HF preferably is diluted with equal to or more than 80% (v/v) of an inert gas, for example, nitrogen or a noble gas, preferably argon. Preferably, the inert gas content is equal to or less than 97.5% (v/v). An especially preferred content of inert gas is in the range of 95±2% (v/v) of inert gas.

In step B), flushing is optionally performed to remove volatiles from the catalyst. It is preferred to perform a flushing step. Flushing can be stopped when the desired degree of purification has been achieved. It can be performed for an extended time, for example, up to ten hours or more. Preferably, flushing is performed for equal to or less than 6 hours. Preferably, it is performed for equal to or more than 1 hour. The temperature during flushing is preferably equal to or higher than 200° C. Preferably, it is equal to or lower than 300° C. A temperature range between 240° C. and 260° C. is very suitable. This is especially advantageous if the activation was performed using HF.

Oxyfluorides on a support can be prepared as described in WO 2006/058794. The process includes a step of converting the precursor into an X-ray amorphous oxide/hydroxyfluoride. This conversion can be performed by hydrolysis or thermal treatment of the precursor if it contains a metal-oxygen bond.

It is to be noted that the manufacture of supported catalysts according to the present invention as described herein is also applicable to other metal fluorides and especially to mixtures of different metal fluorides resulting in doped systems.

The supported catalyst can be prepared in the form of a powder, in the form of pellets, beads, extrudates and other formed bodies. Beads with a diameter in the range of, for example, 1 to 10 mm are very suitable for the dehydrofluorination process.

The terms "hydrochlorofluoroalkanes" and "hydrochlorofluoroalkenes" denote compounds which consist of chlorine, fluorine, hydrogen and carbon; the hydrochlorofluoroalkanes contain at least one chlorine atom and at least two fluorine atoms, the hydrochlorofluoroalkenes contain at least one chlorine atom and at least one fluorine atom. The term "hydrofluoroalkenes" includes compounds which have one, two or more C—C double bonds. The hydrochlorofluoroalkanes and hydrochlorofluoroalkenes can be linear or branched.

The hydrofluorochlorofluoroalkanes and hydrochlorofluoroalkenes have at least 2 carbon atoms. Preferably, they have at least 3 carbon atoms.

Preferred hydrochlorofluoroalkenes and hydrochlorofluoroalkanes have equal to or less than 10 carbon atoms. Very preferably, they have equal to 8 or less than 8 carbon atoms. Especially preferably, they have equal to or less than 6 carbon atoms. Very preferably, they have 3 to 6 carbon atoms.

Preferred hydrochlorofluoroalkenes and hydrochlorofluoroalkanes have 1 to 4 chlorine atoms. Very preferably, they have 1 to 3 chlorine atoms, more preferably, 1 or 2 chlorine atoms. 1 chlorine atom is especially preferred.

Preferred hydrochlorofluoroalkanes have at least 2 fluorine atoms. Very preferably, they have at least 3 fluorine atoms. Preferred hydrochlorofluoroalkenes have at least 1 fluorine atom; very preferably, they have at least 2 fluorine atoms.

Especially preferred hydrochlorofluoroalkanes are those of the general formula (I)

$$C_mClF_nH_{2m+1-n} \quad (I)$$

wherein m is 3 to 6, and n is (m−1) to (2m−1), or of formula (II)

$$C_mCl_2F_nH_{2m-n} \quad (II)$$

wherein m is 3 to 6, n is (m−1) to (2m−2), or of formula (III)

$$C_mCl_3F_nH_{2m-n-1} \quad (III)$$

wherein m is 3 to 6, n is (m−1) to (2m−3), with the proviso that the sum of chlorine atoms, fluorine atoms and hydrogen atoms in the compounds of formulae (I), (II) and (III) is 2 m+2.

The alkenes which can be prepared from the compounds of formulae (I), (II) and (III) have at least 1 atom each of hydrogen and fluorine (it is clear that the number of hydrogen atoms and fluorine atoms split off must be the same) less than the corresponding alkane starting material. Depending on the chain length and the nature of the molecule, 2 or more atoms each of hydrogen and fluorine can be split off.

Hydrochlorofluoropropanes, hydrochlorofluorobutanes and hydrochlorofluoropentanes are especially preferred starting material. Still more preferred starting material are chlorofluoropropanes which are only substituted by chlorine and/or fluorine on the C1 and C3 atom, and hydrochlorofluorobutanes which are only substituted by chlorine and/or fluorine on the C1 and C3 atom while the C2 and in the case of butanes, the C2 and C4 atom are only substituted by hydrogen.

The hydrochlorofluoroalkanes starting compounds are known. They can be prepared by incomplete fluorination of the respective hydrochloroalkanes. For example, they may be side products in fluorination reactions. 3-Chloro-1,1,1,3-tetrafluorobutane can be a side product in a process for the manufacture of 1,1,1,3,3-pentafluorobutane from the respective pentachlorobutane compound. This compound and other chlorofluorobutanes are mentioned, for example, in U.S. Pat. No. 5,739,406 and U.S. Pat. No. 7,074,434. The starting compounds also can be prepared by chlorine-fluorine exchange in hydrochlorofluoroalkanes which have at least one chlorine atom more and at least one fluorine atom less than the desired reaction product. They can also be prepared by addition of HCl to respective hydrofluoroalkenes or hydrochlorofluoroalkenes. In general, the synthesis of the starting compounds is well known in the art. Preferred starting compounds and reaction products are the following:

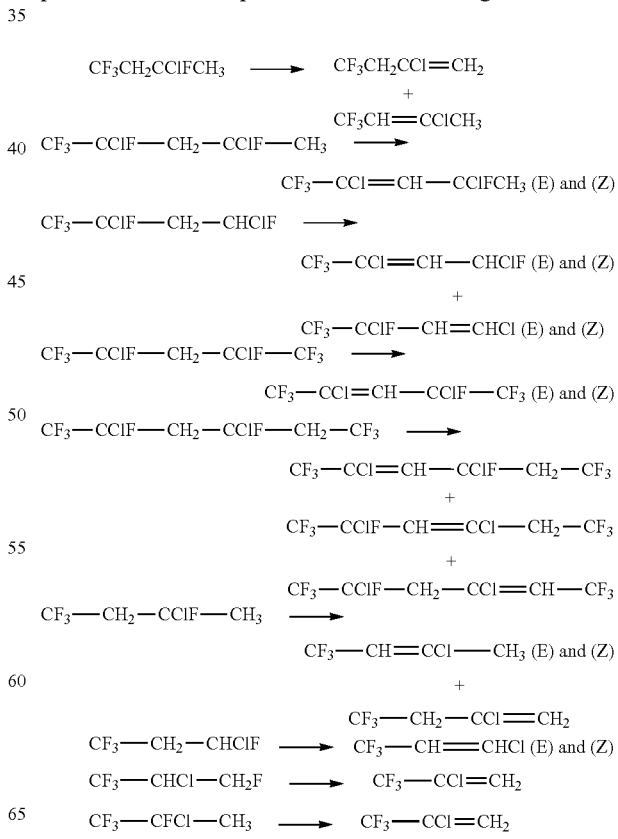

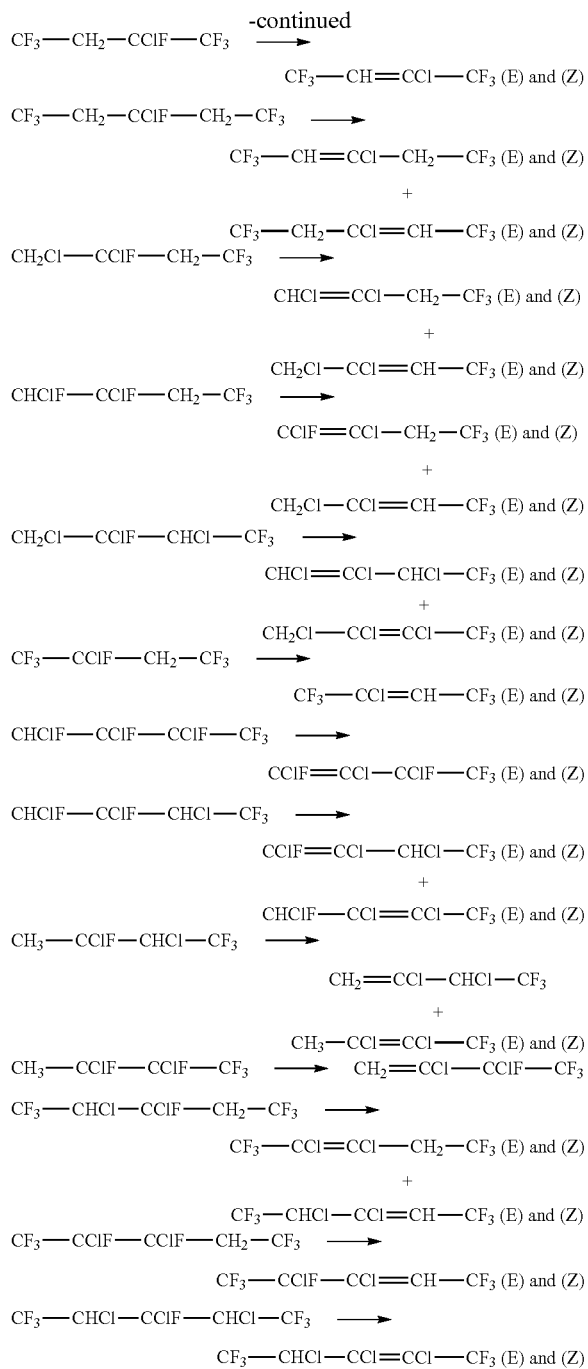

If desired, the dehydrofluorination reaction can be performed in the liquid phase at a pressure and at a temperature where the starting material is present in the liquid phase. The dehydrofluorination reaction is preferably performed in the gas phase. Also here, temperature and pressure are selected such that starting material and reaction products are present in the gas phase during contact with the catalyst.

The dehydrofluorination is performed under conditions which allow a selective reaction at reasonable speed of reaction. A gas phase reaction which is, as mentioned, the preferred type, is preferably performed at a pressure equal to or greater than 0.5 bar (abs.). Preferably, it is performed at a pressure equal to or lower than 10 bar (abs.). It is preferred to perform the dehydrofluorination at a pressure equal to or lower than 2 bar (abs.). It is especially preferred to perform the reaction at a pressure equal to or lower than 1.5 bar (abs.), especially at ambient pressure (about 1 bar). Dehydrofluorination occurs often already at ambient temperature (about 20° C.). The reaction temperature is preferably equal to or higher than 50° C. Preferably, it is equal to or lower than 500° C. More preferably, the reaction temperature during hydrofluorination is equal to or lower than 350° C. Still more preferably, it is equal to or lower than 300° C. The reaction can for example be performed at a temperature from 100 to 250° C. with good yield.

The reaction mixture obtained can be separated in a known manner. Often, the reaction mixture may contain unreacted starting material, HF, the desired hydrochlorofluoroalkene and, sometimes, products resulting from side reactions. For example, the reaction mixture can be scrubbed with water to remove acidic components, for example, HF or HCl. Alternatively, HF can be removed by passing the reaction mixture over sorbents for HF, e.g. KF or NaF. The constituents which are not removed, mostly organic compounds, can be distilled, if desired, under elevated pressure.

The compounds obtained by the process are useful as monomers for preparing chlorofluoropolymers. They also can be used as intermediates in chemical synthesis. They can, for example, be hydrogenated to obtain saturated chlorofluoroalkanes. The compounds obtained in the process of the invention are also suitable per se, e.g. as solvent or refrigerant or as a part thereof.

Another aspect of the present invention concerns novel hydrochlorofluoroalkenes. These are selected from the group consisting of Compounds selected from the group consisting of: $CF_3$—CCl=CH—CClFCH$_3$ (E) and (Z); $CF_3$—CCl=CH—CHClF (E) and (Z); $CF_3$—CClF—CH=CHCl (E) and (Z); $CF_3$—CCl=CH—CClF—$CF_3$ (E) and (Z); $CF_3$—CCl=CH—CClF—$CH_2$—$CF_3$; $CF_3$—CClF—CH=CCl—$CH_2$—$CF_3$; $CF_3$—CClF—$CH_2$—CCl=CH—$CF_3$; CHCl=CCl—$CH_2$—$CF_3$ (E) and (Z); $CH_2Cl$—CCl=CH—$CF_3$ (E) and (Z); CClF=CCl—$CH_2$—$CF_3$ (E) and (Z); $CH_2Cl$—CCl=CH—$CF_3$ (E) and (Z); CHCl=CCl—CHCl—$CF_3$ (E) and (Z); $CH_2Cl$—CCl=CCl—$CF_3$ (E) and (Z); CClF=CCl—CClF—$CF_3$ (E) and (Z); CClF=CCl—CHCl—$CF_3$ (E) and (Z); CHClF—CCl=CCl—$CF_3$ (E) and (Z); CClF=CCl—CClF—$CF_3$ (E) and (Z); $CH_2$=CCl—CHCl—$CF_3$; $CH_3$—CCl=CCl—$CF_3$ (E) and (Z); $CH_2$=CCl—CClF—$CF_3$; $CF_3$—CCl=CCl—$CH_2$—$CF_3$ (E) and (Z); $CF_3$—CHCl—CCl=CH—$CF_3$ (E) and (Z); $CF_3$—CClF—CCl=CH—$CF_3$ (E) and (Z); $CF_3$—CHCl—CCl=CCl—$CF_3$ (E) and (Z).

The advantage of the process of the present invention is that it can be performed at relatively low temperatures, for example, at equal to or less than 350° C. or even 300° C. Even dehydrofluorination at 100 to 250° C. is successful.

The invention will now be explained further in the following examples without any intention of limitation.

EXAMPLES

Example 1

Manufacture of γ-Al$_2$O$_3$ Supported HS-AlF$_3$ 1.1: Manufacture of γ-Al$_2$O$_3$ Supported HS-AlF$_3$ Precursor First, γ-Al$_2$O$_3$ (10 g, pellets 3 mm diameter), calcined at 900° C. in air for 12 hours whereby according to X-ray diffraction analysis no conversion to α-Al$_2$O$_3$ was detectable, was added to a stirred solution of aluminium triisopropoxide (Al(O$^i$Pr)$_3$) (1.2 g) in water free isopropanol (15 mL). Stirring continued for about 0.5 hours, then 18 mMol hydrogen fluoride dissolved in water free isopropanol (6 ml) were added and for about another 1.5 hours stirred. The mixture was then placed in a rotary evaporator and at 70° C. under vacuum the solvent removed yielding about 11 g γ-Al$_2$O$_3$ supported HS-AlF$_3$ precursor.

1.2: Manufacture of γ-Al$_2$O$_3$ Supported HS-AlF$_3$ (HS-AlF$_3$/γ-Al$_2$O$_3$)

Supported precursor prepared according to example 1.1 (about 2 g) was loaded into a vertical stainless steel tube reactor on a silver wool plug. A mixture of CHClF$_2$ (4 mL/min) and N$_2$ (20 mL/min) was passed through the sample and the temperature of the reactor was slowly increased up to 250° C. After altogether 6 hours the reactor was cooled down and about 1.9 g catalyst, corresponding to 4.9% HS-AlF$_3$ loading on the Al$_2$O$_3$, was taken out under exclusion of moisture.

Example 2

Bulk HS-AlF$_3$

Bulk high-surface AlF$_3$ was prepared as described in EP-A-1 440 939.

Example 3

Manufacture of Chlorotrifluorobutene

Apparatus: 25 g of the high-surface AlF$_3$ supported on a carrier, produced as described in example 1, was loaded into a vertical stainless steel tube reactor on a silver wool plug. A mixture of 3-chloro-1,1,1,3-tetrafluorobutane and nitrogen was passed at ambient pressure and at a temperature of 200° C. over the catalyst. The conversion of 3-chloro-1,1,1,3-tetrafluorobutane was 90%.

The reaction mixture was passed through a tower containing NaF to remove HF. The resulting gas mixture was then analyzed by gas chromatography.

The GC analysis revealed the following three dehydrofluorinated products:

| Compound | Relative content in the reaction mixture |
|---|---|
| CF$_3$—CH=CCl—CH$_3$ (E) | 1 |
| CF$_3$—CH=CCl—CH$_3$ (Z) | 1 |
| CF$_3$—CH$_2$—CCl=CH$_2$ | 2 |

The compounds can be separated for example by distillation. They are useful, for example, as intermediates in chemical synthesis. For example, fluorine can be added to produce a chlorofluorobutane having one fluorine atom more than the alkane which had been used as starting material to produce the hydrochlorofluoroalkenes.

Example 4

Manufacture of Chlorotrifluorobutene Using a Bulk Catalyst

Example 3 is repeated using a bulk HS-AlF$_3$ catalyst. CF$_3$—CH=CCl—CH$_3$ (E), CF$_3$—CH=CCl—CH$_3$ (Z) and CF$_3$—CH$_2$—CCl=CH$_2$ are produced in the same ratio as in example 3.

Example 5

Manufacture of Chlorotrifluoropropene Using a Supported Catalyst

Example 3 is repeated. CF$_3$CH$_2$CHClF mixed with nitrogen in a volume ratio of 1:4 is passed over a supported catalyst prepared as described in example 1. CF$_3$CH=CHCl is produced in the form of both isomers, the (E) isomer and the (Z) isomer. These compounds are useful as blowing agents as described in WO 2008/121783.

The invention claimed is:

1. A process for the preparation of one or more hydrochlorofluoroalkenes from a hydrochlorofluoroalkane, comprising contacting said hydrochlorofluoroalkane with a X-ray amorphous high surface metal fluoride, having an active surface of 100-300 m$^2$/g measured with N$_2$, or a X-ray amorphous or weakly crystalline metal oxide fluoride to form one or more hydrochlorofluoroalkenes via a dehydrofluorination reaction, wherein the metal in said metal fluoride or metal oxide fluoride is selected from the group consisting of the 2$^{nd}$ main group, the 3$^{rd}$ main group, the 4$^{th}$ main group, and any subgroup of the periodic system of elements.

2. The process of claim 1 wherein the X-ray amorphous high surface metal fluoride or X-ray amorphous or weakly crystalline metal oxide fluoride is supported on a carrier.

3. The process of claim 1 wherein the metal fluoride is aluminum fluoride, or wherein the metal oxide fluoride is aluminum oxide fluoride.

4. The process of claim 1 wherein one or more hydrochlorofluoroalkenes with 2 to 10 carbon atoms are prepared from corresponding hydrochlorofluoroalkane having 2 to 10 carbon atoms.

5. The process of claim 4 wherein one or more hydrochlorofluoroalkenes with 3 to 8 carbon atoms are prepared from corresponding hydrochlorofluoroalkane having 3 to 8 carbon atoms.

6. The process of claim 5 wherein one or more hydrochlorofluoroalkenes with 3 to 6 carbon atoms are prepared from corresponding hydrochlorofluoroalkane having 3 to 6 carbon atoms.

7. The process of claim 1 wherein the hydrochlorofluoroalkane is substituted by 1 to 3 chlorine atoms and at least 2 fluorine atoms.

8. The process of claim 1 wherein the hydrochlorofluoroalkane is a compound having the general formula selected from the group consisting of formulae (I), (II), and III, said formula (I) being $$C_mClF_nH_{2m+1-n} \qquad (I)$$

wherein m is 3 to 6, and n is (m−1) to (2m−1); said formula (II) being $$C_mCl_2F_nH_{2m-n} \qquad (II)$$

wherein m is 3 to 6, n is (m−1) to (2m−2); said formula (III) being $$C_mCl_3F_nH_{2m-n-1} \qquad (III)$$

wherein m is 3 to 6, n is (m−1) to (2m−3), with the proviso that the sum of chlorine atoms, fluorine atoms and hydrogen atoms in the compounds of formulae (I), (II) and (III) is 2m+2.

9. The process of claim 1 wherein the hydrochlorofluoroalkane is selected from the group consisting of CF$_3$CH$_2$CClFCH$_3$, CF$_3$—CClF—CH$_2$—CHClF, CF$_3$—CClF—CH$_2$—CClF—CH$_3$, CF$_3$—CClF—CH$_2$—CClF—CF$_3$, CF$_3$—CClF—CH$_2$—CClF—CH$_2$—CF$_3$, CF$_3$—CH$_2$—

CClF—CH$_3$, CF$_3$—CH$_2$—CHClF, CF$_3$—CFCl—CH$_3$, CF$_3$—CHCl—CH$_2$F, CF$_3$—CH$_2$—CClF—CF$_3$, CF$_3$—CH$_2$—CClF—CH$_2$—CF$_3$, CH$_2$Cl—CClF—CH$_2$—CF$_3$, CHClF—CClF—CH$_2$—CF$_3$, CHClF—CClF—CClF—CF$_3$, CF$_3$—CClF—CH$_2$—CF$_3$, CH$_2$Cl—CClF—CHCl—CF$_3$CHClF, CClF—CHCl—CF$_3$, CF$_3$—CClF—CHCl—CF$_3$, CHClF—CClF—CClF—CF$_3$, CH$_3$—CClF—CHCl—CF$_3$, CH$_3$—CClF—CClF—CF$_3$, CF$_3$—CHCl—CClF—CH$_2$—CF$_3$, CF$_3$—CClF—CClF—CH$_2$—CF$_3$, CF$_3$—CHCl—CClF—CHCl—CF$_3$, CF$_3$—CClF—CClF—CHCl—CF$_3$, CF$_3$—CHCl—CClF—CClF—CF$_3$, and CF$_3$—CClF—CClF—CHCl—CF$_3$.

10. The process of claim 1 wherein CF$_3$CH$_2$CHClF is reacted to produce CF$_3$CH=CHCl.

11. The process of claim 1 wherein the reaction is performed in the gas phase at a pressure of equal to or higher than 0.5 bar (abs.) and equal to or lower than 2 bar (abs.).

12. The process of claim 1 wherein the reaction is performed at a temperature equal to or greater than 20° C., and equal to or lower than 500° C.

13. The process of claim 12 wherein the reaction is performed at a temperature equal to or greater than 50° C.

14. The process of claim 1 wherein the reaction is performed at a temperature equal to or lower than 350° C.

15. The process of claim 1 wherein said one or more hydrochlorofluoroalkenes are selected from the group consisting of: CF$_3$—CCl=CH—CClFCH$_3$ (E) and (Z); CF$_3$—CCl=CH—CHClF (E) and (Z); CF$_3$—CClF—CH=CHCl (E) and (Z); CF$_3$—CCl=CH—CClF—CF$_3$ (E) and (Z); CF$_3$—CCl=CH—CClF—CH$_2$—CF$_3$; CF$_3$—CClF—CH=CCl—CH$_2$—CF$_3$; CF$_3$—CClF—CH$_2$—CCl=CH—CF$_3$; CHCl=CCl—CH$_2$—CF$_3$ (E) and (Z); CH$_2$Cl—CCl=CH—CF$_3$ (E) and (Z); CClF=CCl—CH$_2$—CF$_3$ (E) and (Z); CH$_2$Cl—CCl=CH—CF$_3$ (E) and (Z); CHCl=CCl—CHCl—CF$_3$ (E) and (Z); CH$_2$Cl—CCl=CCl—CF$_3$ (E) and (Z); CClF=CCl—CClF—CF$_3$ (E) and (Z); CClF=CCl—CHCl—CF$_3$ (E) and (Z); CHClF—CCl=CCl—CF$_3$ (E) and (Z); CClF=CCl—CClF—CF$_3$ (E) and (Z); CH$_2$=CCl—CHCl—CF$_3$; CH$_3$—CCl=CCl—CF$_3$ (E) and (Z); CH$_2$=CCl—CClF—CF$_3$; CF$_3$—CCl=CCl—CH$_2$—CF$_3$ (E) and (Z); CF$_3$—CHCl—CCl=CH—CF$_3$ (E) and (Z); CF$_3$—CClF—CCl=CH—CF$_3$ (E) and (Z); and CF$_3$—CHCl—CCl=CCl—CF$_3$ (E) and (Z).

16. The process of claim 1 wherein CF$_3$CH$_2$CClFCH$_3$ is reacted to form CF$_3$CH$_2$CCl=CH$_2$ and/or CF$_3$CH=CClCH$_3$.

17. The process of claim 1 wherein the metal fluoride is a Lewis-acid metal fluoride selected from the group consisting of aluminium fluorides, chromium fluorides, and iron fluorides.

18. The process of claim 1 for the preparation of one or more hydrochlorofluoroalkenes from a hydrochlorofluoroalkane, comprising contacting said hydrochlorofluoroalkane with a X-ray amorphous high surface metal fluoride, having an active surface of 100-300 m$^2$/g measured with N$_2$, to form one or more hydrochlorofluoroalkenes via a dehydrofluorination reaction, wherein the metal in said metal fluoride or metal oxide fluoride is selected from the group consisting of the 2$^{nd}$ main group, the 3$^{rd}$ main group, the 4$^{th}$ main group, and any subgroup of the periodic system of elements.

19. The process of claim 18 wherein the metal fluoride is a Lewis-acid metal fluoride selected from the group consisting of aluminum fluorides, chromium fluorides, and iron fluorides.

20. The process of claim 19 wherein the metal fluoride is aluminum fluoride.

* * * * *